United States Patent
Otto

(10) Patent No.: US 6,179,869 B1
(45) Date of Patent: Jan. 30, 2001

(54) ARTIFICIAL HEART VALVE

(75) Inventor: Karl-Heinz Otto, Kiel (DE)

(73) Assignee: Tricumed Medizintechnik GmbH (DE)

(*) Notice: Under 35 U.S.C. 154(b), the term of this patent shall be extended for 0 days.

(21) Appl. No.: 09/214,700
(22) PCT Filed: Jun. 10, 1997
(86) PCT No.: PCT/DE97/01226
§ 371 Date: Jan. 8, 1999
§ 102(e) Date: Jan. 8, 1999
(87) PCT Pub. No.: WO98/02115
PCT Pub. Date: Jan. 22, 1998

(30) Foreign Application Priority Data

Jul. 11, 1996 (DE) .............................................. 196 27 859

(51) Int. Cl.[7] ...................................................... A61F 2/24
(52) U.S. Cl. .......................................... 623/2.33; 623/2.28
(58) Field of Search ........................................ 623/2, 900

(56) References Cited

U.S. PATENT DOCUMENTS

| 4,846,830 | * | 7/1989 | Knoch et al. | 623/2 |
| 4,908,028 | * | 3/1990 | Colon et al. | 623/2 |
| 5,326,372 | * | 7/1994 | Mhatre et al. | 623/2 |

\* cited by examiner

Primary Examiner—David H. Willse

(57) ABSTRACT

Prosthesis for the replacement of heart valves, with a valve ring (10) with a radius R, in which at least two substantially elongated wing valves (12, 14, 16) are mounted so as to rotate about in each case an axis (18) located in the ring plane, the axes (18) in the projection on the ring plane having a distance of 0.5 R to 0.9 R from the center of the ring plane and the edges of the inwardly directed portions engage in flush manner on the edges of the corresponding portions of the other wing valves (12, 14, 16) and in the area (20) of the wing valves (12, 14, 16) pointing in the flow direction in the opened state thereof, said valves are provided with a bevel (24), constructed as a sharp break-away edge (22), running from the outside to the inside in the flow direction.

4 Claims, 2 Drawing Sheets

ARTIFICIAL HEART VALVE

BACKGROUND OF THE INVENTION

Field of the Invention

The invention relates to a heart valve prosthesis used for the replacement of natural heart valves and more particularly to an artifical heart valve with a valve ring in which three wing valves are mounted.

In the subsequently published DE 195 32 973 C1 a heart valve is proposed having the features of the preamble of claim 1, in which the surface of the wing valves which is outwardly directed in the opened state is given a continuously curved construction and the axes are outwardly displaced with respect to the body of the wing valves. EP 283 413 Al discloses a similarly constructed valve, in which the area directed in the flow direction forms a bevel running from the outside to the inside. The axis of the wing valves passes through the body thereof.

SUMMARY OF THE INVENTION

The construction according to DE 195 32 973 has the advantage that the flow resistance is low, but the disadvantage of an inadequate closing behaviour.

The problem of the invention Is to so further develop the known heart valve, that in the case of a limited flow resistance it has a good closing behaviour.

According to the invention this problem is solved by a prosthesis for the replacement of heart valves, with a valve ring with a radius R, in which three wing valves are mounted in rotary manner about in each case an axis located in the ring plane, in which the axes in the projection on the ring plane have a distance of 0.5R to 0.9R form the center of the ring plane, the axes, considered in the central flow direction, are outwardly displaced with respect to the body of the wing valves, the edges of the inwardly directed portions, in the closed state, engage flush on the edges of the corresponding portions of the other wing valves, the faces of the wing valves directed inwards in the opened state, are substantially elongated, and the faces of the wing valves, directed outwards in the opened state, in their area pointing in the central flow direction are provided with a bevel passing from the outside to the inside and which in the closed state of the valve extends from the center of the ring plane over 0.2 to 0.5 R. A preferred embodiment of the invention provides that in their area directed against the flow direction in the opened state, the wing valve are rounded.

The invention is described in greater detail hereinafter relative to the attached drawings, wherein show:

DETAILED DESCRIPTION OF PREFERRED EMBODIMENTS

Figure 1:
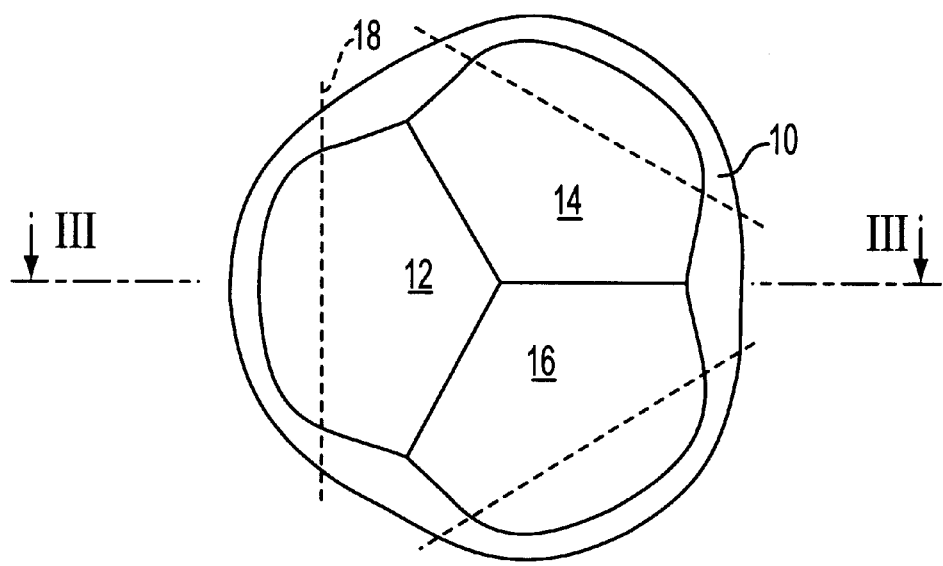
FIG. 1 A plan view of the heart valve prosthesis with the valves closed.

The prosthesis for the replacement of heart valves shown in plan view in FIG. 1 is provided with a valve ring 10, which has a radius R. Three wing valves 12, 14, 16 are mounted in the valve ring 10 in each case about a swivel axis 18 running in the ring plane. The distance from the swivel axis to the centre of the ring plane, in the projection on the ring plane, has a distance of 0.5 R to 0.9 R. In the closed state the wing valves 12, 14, 16 with their curved part terminate flush with the ring boundary. At the straight boundaries thereof they terminate flush with the adjacent wing valves 12, 14, 16 and form with the latter a tripod.

The valve ring 10 receiving the axis 18 of the wings and which is fitted to the valve border for sewing into the aorta, can be circular or can have a shape, similar to a triangle and corresponding to the anatomy.

Figure 2:
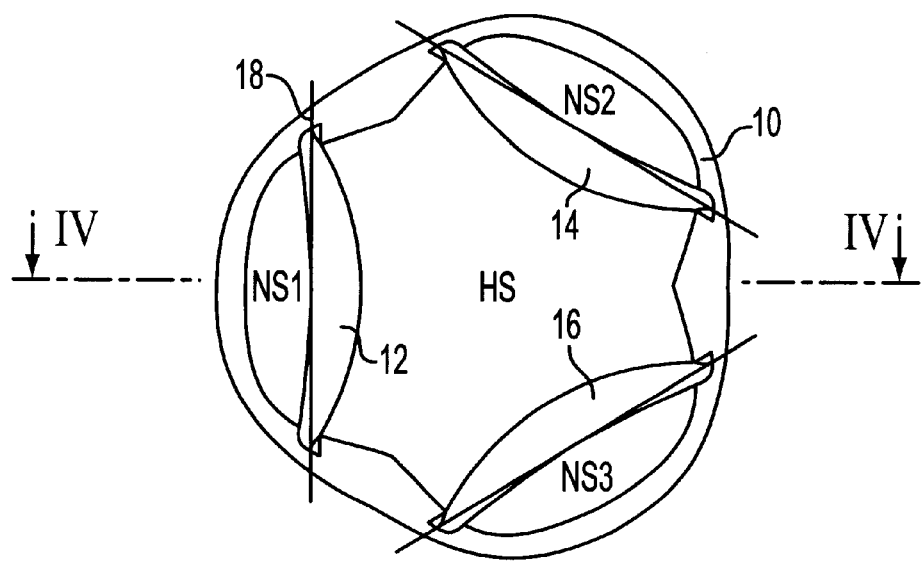
FIG. 2 A plan view of the heart valve prosthesis in the opened state.
Figure 3:
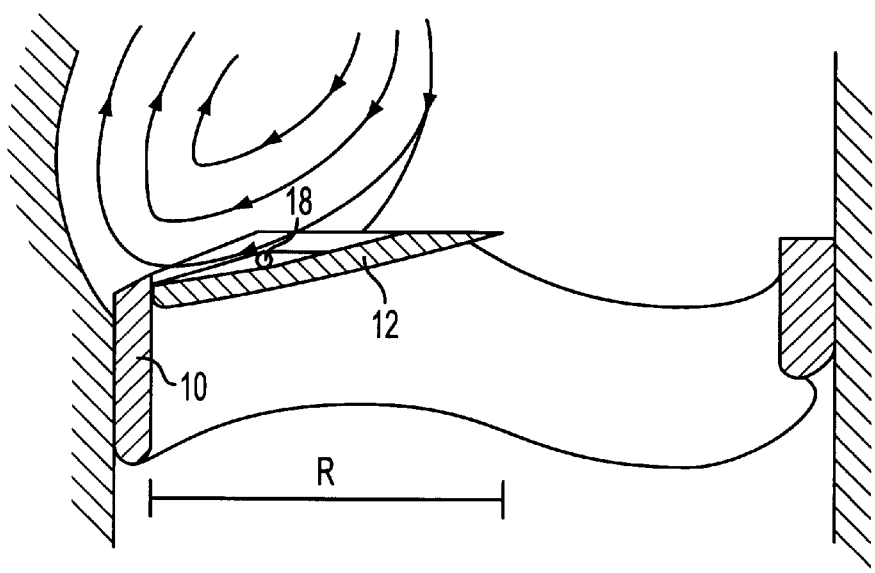
FIG. 3 A section along line III—III in FIG. 1.
Figure 4:
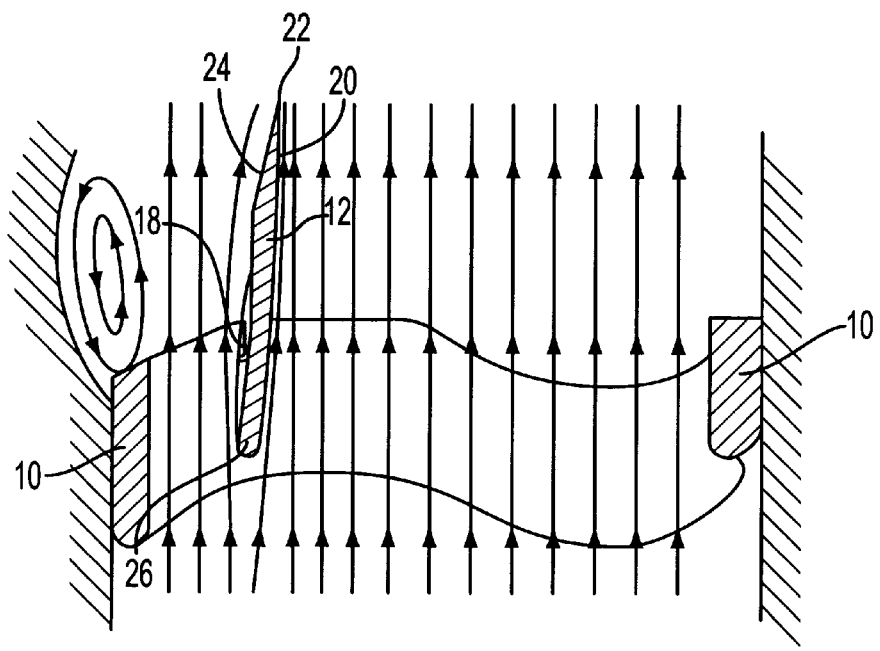
FIG. 4 A section through the heart valve in the state shown in FIG. 2, along line IV—IV.

In FIG. 2, where the valves are opened, it can be seen that there is a large central flow, which is bounded by the convex boundaries of the wing valves. The large cross-section of the area bounded by the inner faces of the wing valves 12, 14, 16 permits a high main flow rate. The flow gradients in the rain flow HS and the three secondary flows NS1, NS2, NS3 outside the wing valves 12, 14, 16 are minimized.

In the ring plane the valve ring 10 is curved in such a way that it largely corresponds to the anatomy of the fitting environment. In the vicinity of the mounting of the axes or pins 18 the valve ring 10 is raised, in order to give the bearings 18 the necessary stability and form a stop for the wing valves 12, 14, 16 in the opened state thereof.

The wing valves 12, 14, 16 are constructed in a substantially elongated manner, but the portion of the valve directed against the flaw direction in the systole (i.e. with the wing valve opened) is slightly outwardly bent with respect to the portion pointing in the flow direction, accompanied by the formation of a concave angle when seen from the axis of symmetry of the prosthesis. This construction, at the end of the systole, brings about an early occurrence of a torque acting in a closing direction.

In order to reduce turbulence, which increases the flow resistance, at the systole (i.e. with the valve opened), in their area 26 directed against the flow direction the wing valves are rounded and in their area 20 directed in the flow direction provided with a bevel 24, which forms a sharp break-away edge 22, where the flow is broken off without the formation of significant turbulence.

In order to ensure a good closing behaviour of the valves, the bevel 24 passes from the outside to the inside in the flow direction, so that in the axial projection a surface is formed, against which flows the blood flowing back into the diastole and thereby exerts on the valve an inwardly directed moment initiating valve closure. The axes 18 are outwardly displaced with respect to the body of the wing valves 12, 14, 16 (seen from the axis of symmetry of the valve), so that said effect is reinforced.

The bevel 24 of the surfaces of the wing valves 12, 14, 16 directed outwards in the opened state, in the closed state of the valve, extends from the centre of the ring plane over 0.2 to 0.5 R.

What is claim is:

1. Prosthesis for the replacement of heart valves, with a valve ring (10) with a radius R, in which three wing valves (12 14, 16) are mounted in rotary manner about in each case an axis (18) located in a ring plane of the valve ring, in which:

the axes (18) in a projection on the ring plane have a distance of 0.5 R to 0.9 R from the center of the ring plane, the axes (18), considered in a central flow direction, are outwardly displaced with respect to the body of the wing valves (12, 14, 16);

edges of a inwardly directed portions of the wing valve, in the closed state of the valve, engage flush on edges of corresponding portions of the other wing valves (12, 14, 16), faces of the wing valves (12, 14, 16), directed inwards in the opened states, are substantially elongated and faces of the wing valves (12, 14, 16), directed outwards in the opened state, in an area pointing in the central flow direction are provided with a bevel (24) passing from the outside to the inside and which in the closed state of the valve extends from the center of the ring plane over 0.2 to 0.5 R.

2. Prosthesis according to claim 1, characterized in that in an area (26) directed against the central flow direction in the opened state, the wing valves (12, 14, 16) are rounded.

3. Prosthesis according to claim 1, wherein a portion of the valve directed against the central flow direction, with the wing valve opened, is slightly outwardly bent with respect to a portion pointing in the central flow direction, forming a concave angle.

4. Prosthesis according to claim 1 wherein in the area (20) directed in the central flow direction the bevel (24) forms a sharp break-away edge (22).

\* \* \* \* \*